US006416787B1

(12) United States Patent
Truter et al.

(10) Patent No.: US 6,416,787 B1
(45) Date of Patent: *Jul. 9, 2002

(54) QUICK RELEASE COMPOSITIONS

(75) Inventors: Patricia-Ann Truter; Emilia Dimitrova Dilova, both of Gauteng Province; Thilo Lothar van der Merwe, Brakpan, all of (ZA)

(73) Assignee: Implico B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,957

(22) PCT Filed: Jul. 1, 1998

(86) PCT No.: PCT/EP98/04073
§ 371 (c)(1),
(2), (4) Date: Feb. 28, 2000

(87) PCT Pub. No.: WO99/01108
PCT Pub. Date: Jan. 14, 1999

(30) Foreign Application Priority Data

Jul. 1, 1997 (ZA) .................................. 97/5853

(51) Int. Cl.⁷ .............................. A61K 9/14; A61K 9/50
(52) U.S. Cl. ....................... 424/489; 424/499; 424/501; 424/502
(58) Field of Search ................................ 424/400, 489, 424/499, 501, 502

(56) References Cited

U.S. PATENT DOCUMENTS

| 3,493,652 A | * | 2/1970 | Hartman ..................... 424/94 |
| 4,855,326 A | | 8/1989 | Fuisz ......................... 514/777 |
| 5,073,379 A | | 12/1991 | Klimesh et al. ............. 242/467 |
| 5,178,878 A | * | 1/1993 | Wehling et al. ............. 424/466 |

FOREIGN PATENT DOCUMENTS

| EP | 0 576 983 A1 | 1/1994 |
| WO | WO 97/06786 | 2/1997 |

OTHER PUBLICATIONS

Le Hir, Abrégé de Pharmacie Galénique, formes pharmaceutiques, Masson, 1983, pp. 36–42, 168, 169 (and English translantion entitled: Excipients and Packaging Materials).

* cited by examiner

*Primary Examiner*—Thurman K. Page
*Assistant Examiner*—S. Tran
(74) *Attorney, Agent, or Firm*—Frommer Lawrence & Haug LLP; William S. Frommer; Mark W. Russell

(57) ABSTRACT

A dosage form comprises a porous extrudate. The extrudate is obtained by extruding, at elevated temperature, a composition comprising a starch, water, a thermostable enzyme, and a pharmaceutically active agent. The porous extrudate is capable of disintegration when exposed to an aqueous environment.

9 Claims, No Drawings

QUICK RELEASE COMPOSITIONS

This application is a 371 of PCT/EP98/04073 filed Jul. 1, 1998.

THIS INVENTION relates to a quick-release composition. In particular, it relates to a method of making a water-dispersable composition, to an extrudable composition and to a dosage form suitable for the quick delivery in an aqueous environment such as the mouth, of an adjunct such as a medicine, flavourant, or the like.

According to a first aspect of the invention there is provided a method of making a water-dispersable composition, the method including admixing together a polysaccharide, an enzyme capable of splitting the polysaccharide into smaller portions thereof, and a liquid, to form an admixture;

extruding the admixture at an elevated temperature to form an extrudate; and cooling the extrudate, with the liquid evaporating from the extrudate as it cools, thereby forming a porous composition capable of disintegration when exposed to an aqueous environment.

The water-dispersable composition may be a quick-release composition, and may thus be capable of rapid disintegration when exposed to an aqueous environment.

By "quick-release composition" is meant a composition which will disintegrate rapidly, i.e. within 2 minutes when saturated with water; and the constituents, and the proportions thereof, should be selected by routine experimentation, to achieve this object.

According to a second aspect of the invention, there is provided a method of making a water-dispersable quick-release composition, the method including extruding an at least partially destructurised starch at an elevated temperature in the presence of a blowing agent to form an extrudate; and cooling the extrudate to form a porous composition capable of rapid disintegration when exposed to an aqueous environment.

The at least partially destructurising of the starch may be by means of the elevated temperature at which the extrusion is effected, by means of an enzyme capable of splitting the starch, by means of an acid or a base, or by a combination of two or more of these methods.

The partially destructurised starch may be in admixture with a pharmaceutically active agent or an adjunct. The blowing agent may be water.

The method may include admixing a pharmaceutically active agent into the admixture prior to or during the extrusion of the admixture.

Cooling the extrudate may include allowing the extrudate to cool at room temperature.

The method may include admixing an adjunct, such as a flavourant or the like, into the admixture prior to or during the extrusion of the admixture. More particularly, the adjunct may be selected from the group consisting of a flavourant, a preservative, an anti-oxidant, a surfactant, a colouring agent, a pH modifier, a sweetener, a taste masking agent, a plasticizer, a porosity modifying agent, or two or more thereof. The flavourant, when present, may be a mint flavourant, a lemon flavourant, an orange flavourant, a caramel flavourant, a vanilla flavourant, or the like. The pH modifier, when present, may be citric acid, tartaric acid, or the like. The taste masking agent, when present, may be sodium bicarbonate, an adsorbate, or the like, The plasticizer, when present, may be soya bean oil, polyethylene glycol, polyoxyethylene mono stearate, a light mineral oil, or an at least partially hydrated vegetable oil.

The polysaccharide may be starch and the liquid may be water, which may act as a blowing agent. The enzyme may be of the type which requires an aqueous environment to render it capable of splitting the starch.

The method may include cutting the extrudate, eg with a die face cutter, to provide discs or tablets or rods of the quick-release composition.

The starch and the enzyme may be initially present in the admixture, in a mass ratio of starch:enzyme from 10000;1 to 10:1. Preferably, the mass ratio of the starch to the enzyme in the admixture is from 10000:3 to 100:1, and most preferably, the mass ratio of the starch to the enzyme in the admixture is from 10000:5 to 1000:5.

The starch may be selected from the group consisting of corn starch, rice starch, wheat starch, oat starch, potato starch, or two or more thereof.

The water may be added to the admixture during the extruding by means of a pump. The water and starch may be Initially present, in the admixture, in a mass ratio of water:starch of 20:80 to 55:45. Preferably, the Initial mass ratio of the water to starch in the admixture is from 20:80 to 50:50, and most preferably, the initial mass ratio of the water to starch in the admixture is from 20:30 to 40:60, e.g. 30:70.

The polysaccharide or starch forms a carrier or excipient for the adjunct, and the carrier may also include sweeteners, e.g. sugars such as sucrose, dextrose, galactose and lactose. The sweetener may also be aspartame. Thus, the method may include adding a sugar to the admixture.

The enzyme is preferably a thermostable enzyme, such as the enzymes available in South Africa under the trade names THERMAMYL 120L and THERMAMYL 60 DT available from Enzymes South Africa (Proprietary) Limited, and manufactured by Novo Industri A/S, Denmark.

The pharmaceutically active agent may be a drug, such as theophylline, prochlorperazine maleate, paracetamol, or loperamyd, a vitamin such as vitamin A, B, C, D or E, and/or a mineral salt, such as calcium lactate, calcium phosphate, magnesium carbonate or magnesium lactate. The pharmaceutically active agent may function as an antacid, an antidepressant, an antihypertensive, an antimigraine, a hormone, or a urinary agent. The adjunct may be micro-encapsulated, so that It is substantially water-insoluble but soluble in the gut of a mammal, to mask the taste of the adjunct.

The elevated temperature at which the extruding of the admixture may be effected is from 80° C. to 135° C., preferably from 90° C. to 120° C. and most preferably from 100° C. to 120° C., e.g. 110° C.

Typically, extrusion of the admixture is with a screw extruder such as a twin-screw extruder, having a screw speed of from 50 to 200 rpm. The die cutter typically has a cutter speed of from 20 to 100 rpm. eg from 50 to 80 rpm and a diameter size of from 2 to 8 mm.

According to a third aspect of the invention, there is provided an extrudable composition comprising, in admixture with each other, a polysaccharide, a blowing agent and an enzyme capable of splitting the polysaccharide into smaller portions thereof.

The polysaccharide may be starch and the blowing agent may be water. The admixture may include a pharmaceutically active agent.

The composition may include an adjunct, which may be as hereinbefore described.

The enzyme may be present in the admixture at a concentration of from 0.01 to 10% m/m, based on the total admixture mass. Preferably, the concentration of the enzyme in the admixture is from 0.03 to 1% m/m, based on the total admixture mass, and most preferably, the concentration of the enzyme in the admixture is from 0.05 to 0.5% m/m, based on the total admixture mass, e.g. 0.1% m/m based on the total admixture mass.

The enzyme, starch and adjunct may be as hereinbefore described. The pharmaceutically active agent may be present in a concentration of up to 60% m/m, based on the total admixture mass.

The pharmaceutically active agent may be micro-encapsulated, so that it is substantially water-insoluble but dissolves when ingested by a mammal.

The admixture may include a sugar, such as dextrose, galactose and lactose or an artificial sweetener such as aspartame, The invention extends to a dosage form obtained by extruding, at elevated temperature, an admixture comprising a pharmaceutically active agent and the extrudable composition as hereinbefore described.

The dosage form may have a diameter of from 5 to 10 mm and may comprise from 2 to 50 mg of the pharmaceutically active agent.

The pharmaceutically active agent may be as hereinbefore described.

The invention will now be described, by way of example, with reference to the following worked example.

EXAMPLE 2 kg of a polysaccharide in the form of AMYRAL corn starch of a moisture content of 10% by mass was mixed with 0.1% by mass (based on the corn starch) of THERMAMYL 120L enzyme, capable of splitting the polysaccharide molecules of the corn starch into smaller portions thereof, and immobilized on carboxy methylcellulose. The mixture also contained, based on the corn starch, 0.5% by mass soya bean oil as plasticizer, 10% by mass lactose for enhancing the porosity of the eventual product, and 10% by mass of a pharmaceutically active agent.

All the ingredients, with the exception of the enzyme, were premixed in a high-speed mixer for a period of 10 minutes, after which the enzyme was added thereto. The mixture was fed to a hopper of a twin-screw extruder having an extrusion screw speed of 200 rpm, a feed screw speed of 200 rpm and a moisture setting of 20% by mass (setting number 5 on the extruder) with a barrel temperature for the extruder of 110–120° C., and a die of 3 mm diameter.

An extrudate was obtained which was cut into pellets with a die face cutter, the cut pellets then being air-dried on a moving transport belt. The pellets were found to have a uniformly porous structure, and when inserted into the mouth were found to have a wetting time of no more than a few seconds, and a disintegration time of slightly more than 1 minute.

It is an advantage of the invention, as exemplified, that the solubility or dispersability of the dosage form In water can be tailor-made for a particular purpose by the admixing of an enzyme with the starch, so that it can easily and rapidly disintegrate in saliva in a person's mouth. It is a further advantage of the invention that the composition and dosage form are starch-based, and thus not animal-derived. It is yet a further advantage of the invention, as exemplified, that the porosity of the dosage form can be controlled by the addition of a porosity modifying agent such as lactose.

What is claimed is:

1. A dosage form which consists essentially of a porous extrudate obtained by extruding, at a temperature from 80° C. to 135° C., a composition comprising a starch, water, a thermostable enzyme, which is capable of splitting the starch into smaller portions and which requires an aqueous environment to render it capable of splitting the starch, and a pharmaceutically active agent, wherein the starch and the enzyme are initially present in the composition in a mass ratio of starch:enzyme of from 10000:1 to 10:1, with the porous extrudate being capable of disintegration when exposed to an aqueous environment.

2. A dosage form according to claim 1, in which the enzyme is present, in the composition, at a concentration of from 0.05% to 0.5% m/m, based on the total composition mass.

3. A dosage form according to claim 1, in which the starch is selected from the group consisting of corn starch, rice starch, wheat starch, oats starch, potato starch, and two or more thereof.

4. A dosage form according to claim 1, in which the water and starch are present, in the composition, in a mass ratio of water-starch of 20:80 to 40:60.

5. A dosage form according to claim 1, which includes an adjunct selected from the group consisting of a flavorant, a preservative, an antioxidant, a surfactant, a coloring agent, a pH modifier, a sweetener, a taste masking agent, a plasticizer, a porosity modifying agent, and two or more thereof.

6. A dosage form according to claim 1, in which the pharmacetically active agent is present in a concentration of up to 60% m/m, based on the total mass of the dosage form.

7. A dosage form according to claim 1, in which the pharmaceutically active agent is micro-encapsulated so that it is substantially water-insoluble but dissolves when ingested by a mammal.

8. A dosage form according to claim 1, which has a diameter of from 5 to 10 mm and comprises from 2 to 50 mg of the pharmaceutically active agent.

9. A dosage form according to claim 1, in which the starch and the enzyme are initially present, in the composition, in a mass ratio of starch:enzyme of from 10000:5 to 1000:5.

* * * * *

UNITED STATES PATENT AND TRADEMARK OFFICE
CERTIFICATE OF CORRECTION

PATENT NO. : 6,416,787 B1
DATED : July 9, 2002
INVENTOR(S) : Patricia-Ann Truter et al.

It is certified that error appears in the above-identified patent and that said Letters Patent is hereby corrected as shown below:

Column 4,
Line 41, change "pharmacetically" to -- pharmaceutically --.

Signed and Sealed this

Twenty-seventh Day of August, 2002

Attest:

Attesting Officer

JAMES E. ROGAN
*Director of the United States Patent and Trademark Office*